US006999611B1

(12) United States Patent
Lopez et al.

(10) Patent No.: US 6,999,611 B1
(45) Date of Patent: Feb. 14, 2006

(54) RETICLE DEFECT DETECTION USING SIMULATION

(75) Inventors: Daniel Lopez, Menlo Park, CA (US); Frank Schellenberg, Palo Alto, CA (US)

(73) Assignee: KLA-Tencor Corporation, San Jose, CA (US)

( * ) Notice: Subject to any disclaimer, the term of this patent is extended or adjusted under 35 U.S.C. 154(b) by 617 days.

(21) Appl. No.: 09/249,728

(22) Filed: Feb. 13, 1999

(51) Int. Cl.
G06K 9/00 (2006.01)
(52) U.S. Cl. .................. 382/144; 382/145; 382/143
(58) Field of Classification Search ............ 382/144, 382/145, 147, 149, 282, 283, 205; 430/5, 430/22, 30; 703/5
See application file for complete search history.

(56) References Cited

U.S. PATENT DOCUMENTS

| | | | | |
|---|---|---|---|---|
| 5,475,766 A | * | 12/1995 | Tsuchiya et al. | 382/144 |
| 5,619,429 A | * | 4/1997 | Aloni et al. | 700/279 |
| 5,965,306 A | * | 10/1999 | Mansfield et al. | 403/5 |
| 6,016,357 A | * | 1/2000 | Neary et al. | 382/144 |
| 6,171,731 B1 | * | 1/2001 | Medvedeva et al. | 430/5 |
| 6,223,139 B1 | * | 4/2001 | Wong et al. | 703/5 |

OTHER PUBLICATIONS

Budd et al, "Development and Application of a New Tool for Lithographic Mask Evaluation, the Stepper Equivalent Aerial Image Measurement System (AIMS)", 1997, IBM Journal of Research and Development, vol. 41, No. 1/2.*

* cited by examiner

Primary Examiner—Vikkram Bali
(74) Attorney, Agent, or Firm—Mitchell Silberberg & Knupp LLP

(57) ABSTRACT

Defects are detected in a reticle used in integrated circuit chip fabrication by obtaining digital image data corresponding to an image of the reticle. Typically, this is accomplished by scanning the reticle using a laser scanner. The digital image data are then processed according to predetermined criteria to identify defects. Such processing may include, for example, processing the digital image data in comparison to reference digital image data for the same or a similar portion of the reticle. Next, a response that would be produced if the reticle were to be utilized in a photolithographic system is simulated by processing the digital image data corresponding to the reticle.

22 Claims, 3 Drawing Sheets

RETICLE DEFECT DETECTION USING SIMULATION

BACKGROUND OF THE INVENTION

1. Field of the Invention

The present invention relates to detection of defects in reticles used in the fabrication of integrated circuit chips. In particular, the invention concerns reticle defect detection using simulation of a photolithographic system.

2. Description of the Prior Art

Integrated circuits are made by photolithographic processes which use photomasks or reticles and an associated light source to project a circuit image onto a wafer. The light interacts with resist materials on the wafer to define various shapes and channels on the wafer. Then, after appropriate processing, the shapes and channels eventually define the electronic circuits on the wafer. Thus, reticles are used in the semiconductor manufacturing industry for the purpose of transferring photolithographic patterns onto a substrate, typically the wafer, during the manufacture of integrated circuits on the substrate. The wafer may be comprised of silicon, gallium arsenide or the like. In addition, photolithography is used to transfer patterns onto metal layers deposited on semiconductor substrates.

In the semiconductor industry, reticles are typically comprised of a polished transparent substrate, such as a fused quartz plate, on which a thin patterned opaque layer, consisting of figures, has been deposited on one surface. Usually, the patterned opaque layer is chromium. This layer may have a light anti-reflection coating deposited on one or both surfaces of the chromium.

In order to produce functioning integrated circuits at a high yield rate, the reticles need to be free of defects or, at least, free from defects that would adversely affect the photolithographic process or the resulting integrated circuit. A defect may be defined as any unintended modification to the intended photolithographic pattern caused during the manufacture of the reticle or as a result of the use of the reticle.

The following are a few of the possible defects: a portion of the opaque layer being absent from an area where it is intended to be present; a portion of the opaque layer being present in an area where it is not intended to be; chemical stains or residues from the reticle manufacturing processes causing an unintended localized modification of the light transmission property of the reticle; particulate contaminates such as dust, resist flakes, skin flakes; erosion of the photolithographic pattern due to electrostatic discharge; artifacts in the reticle substrate such as pits, scratches, and striations; and localized light transmission errors in the substrate or opaque layer. During the manufacture of reticles, inspection of the reticle is performed in order to detect the aforementioned and other defects.

Automated mask inspection systems have existed for many years. The earliest such system, the Bell Telephone Laboratories AMIS system (John Bruning et al., "An Automated Mask Inspection System—AMIS", IEEE Transactions on Electron Devices, Vol. ED-22, No. 7 July 1971, pp 487 to 495), used a laser that scanned the mask. Subsequent systems used a linear sensor to inspect an image projected by the mask, such as described by Levy et al. in U.S. Pat. No. 4,247,203, "Automatic Photomask Inspection System and Apparatus" who teach die-to-die inspection, i.e., inspection of two adjacent dies by comparing them to each other. Alternately, in U.S. Pat. No. 4,926,489, ("Reticle Inspection System") Danielson et al. teach die-to-database inspection, i.e. inspection of the reticle by comparison to the database containing data regarding the intended design from which the reticle was made. U.S. Pat. Nos. 4,247,203 and 4,926,489 are incorporated herein by reference as though set forth herein in full.

A first type of defect detection method is the die-to-die method. In this method, a first reticle is scanned by laser or other light source and the image of the first reticle is projected onto a sensor which reads the image. The image detection process is repeated for a second reticle where the second reticle is identical in design to the first reticle. Then, the resulting image of the first reticle is compared with the resulting image of the second reticle to detect defects. Typically, the second reticle is adjacent to the first reticle on the same wafer.

Another type of defect detection method is the die-to-database method. In this method, the first reticle is scanned, and the resulting image is compared to the information contained in the database defining the first reticle, in order to detect defects. Typically, the database is a CADS (Computer Aided Design System) containing the information used to create the reticle under examination. In such a case, the CADS database is converted to an image format before being compared to the scanned image of the first reticle. See U.S. Pat. No. 4,926,489, which is incorporated herein by reference as though set forth herein in full.

Both the die-to-die and die-to-database techniques typically involve performing predetermined methods for comparing the subject image data to the reference image data, and then identifying any substantial differences. This may be accomplished by actually calculating a difference image or else by comparing features of the two images. Generally, defect detection is performed automatically using a programmed computer workstation. The output of the software typically is a list of the identified defects, together with images of those defects.

The above-discussed defect detection methods thus provide reports of the defects of the reticle under examination, but do not provide much information to determine the printability of the defect. That is, the defect report itself does not provide sufficient information to determine whether or not each of the defects is likely to cause negative impact on the lithography process or to adversely affect the device performance. Currently, this determination usually is made exclusively by human operators examining each of the defects that were detected using the above-discussed processes. Determining defect printability in this manner generally is very time-consuming, inconsistent, and inaccurate because it relies purely on the human operator's experience and intuition. Typically, in each case the operator must use his judgment in determining, based on the defect size, type and location relative to patterns on the reticle, whether the defect is likely to cause a significant problem when the reticle is used in chip fabrication.

Errors in evaluating defect printability can be costly. For example, rather than risk a return of the reticle, mask shops often choose to clean or repair reticles when defects are found. If the defect would not in fact have printed as the operator predicted, such cleaning and repair introduces unnecessary delays and costs. In addition, unnecessary repair is risky because it may introduce serious defects which themselves can be irreparable, requiring the reticle to be scrapped. On the other hand, defects that are incorrectly judged to be inconsequential will show up later during fabrication, causing additional fabrication delays and expense.

Moreover, as the complexity of integrated circuits increases and feature sizes decrease, the number of defects has been increasing. This has occurred for a number of reasons. For example, higher resolution photolithography means that smaller defects are printable; as the image pixel size decreases, more defects become visible; also defect specification are becoming tighter. As a result, the number of defects per reticle has increased up to 800. It is noted that when optical proximity correction (OPC) is used, the sub-resolution sizes of the serifs and other elements of the reticle can compound the problem.

The foregoing developments have increased the demands on the inspection process. Both the need for resolving smaller defects and for inspecting larger areas are requiring much greater speed requirements, in terms of number of elements processed per second. Accordingly, it is becoming increasingly important to provide additional objective information for determining defect printability.

It therefore would be advantageous to automate or mechanize the defect printability determination by ascertaining the impact of each of the defects on the lithography process or device performance. Such a system or process would allow for early detection and repair of defects of reticles. Moreover, the system or the process would reduce the heavy reliance on human intuition and experience, and increase the confidence and reliability in the printability of reticles; thereby increasing the production yield of good circuits from the semiconductor wafers.

SUMMARY OF THE INVENTION

The present invention addresses the foregoing need by detecting reticle defects and then performing a lithography simulation of digital image data for the reticle.

Thus, in one aspect, the invention detects defects in a reticle used in integrated circuit chip fabrication by first obtaining digital image data corresponding to an image of the reticle. Typically, this is accomplished by scanning the reticle using a laser scanner. The digital image data are then processed according to predetermined criteria to identify defects. Such processing may include, for example, processing the digital image data in comparison to reference digital image data for the same or a similar portion of the reticle. Next, a response that would be produced if the reticle were to be utilized in a photolithographic system is simulated by processing the digital image data corresponding to the reticle.

By virtue of the foregoing arrangement, the present invention can provide a user with additional information regarding an identified defect, and in particular, information such as how the defect is likely to print on the wafer. With this additional information, a user generally will be more likely to make an accurate assessment regarding the significance of the defect. As a result, the present invention often can help avoid unnecessary re-works and at the same time identify truly problematic defects earlier, thereby reducing delays and costs.

According to a further aspect of the invention, a reference portion of a reticle also may be subject to simulation processing, giving the user a baseline for comparison. In still further aspects, the invention also may include automatic categorizations of defects based on the simulation results, thereby further reducing the chances for operator error. In still further aspects, the invention only simulates windows around identified defects, thereby reducing the required simulation processing.

The foregoing summary is intended merely to provide a brief description of the general nature of the invention. A more complete understanding of the invention can be obtained by referring to the claims and the following detailed description of the preferred embodiments in connection with the accompanying figures.

DESCRIPTION OF THE PREFERRED EMBODIMENTS

Figure 1:
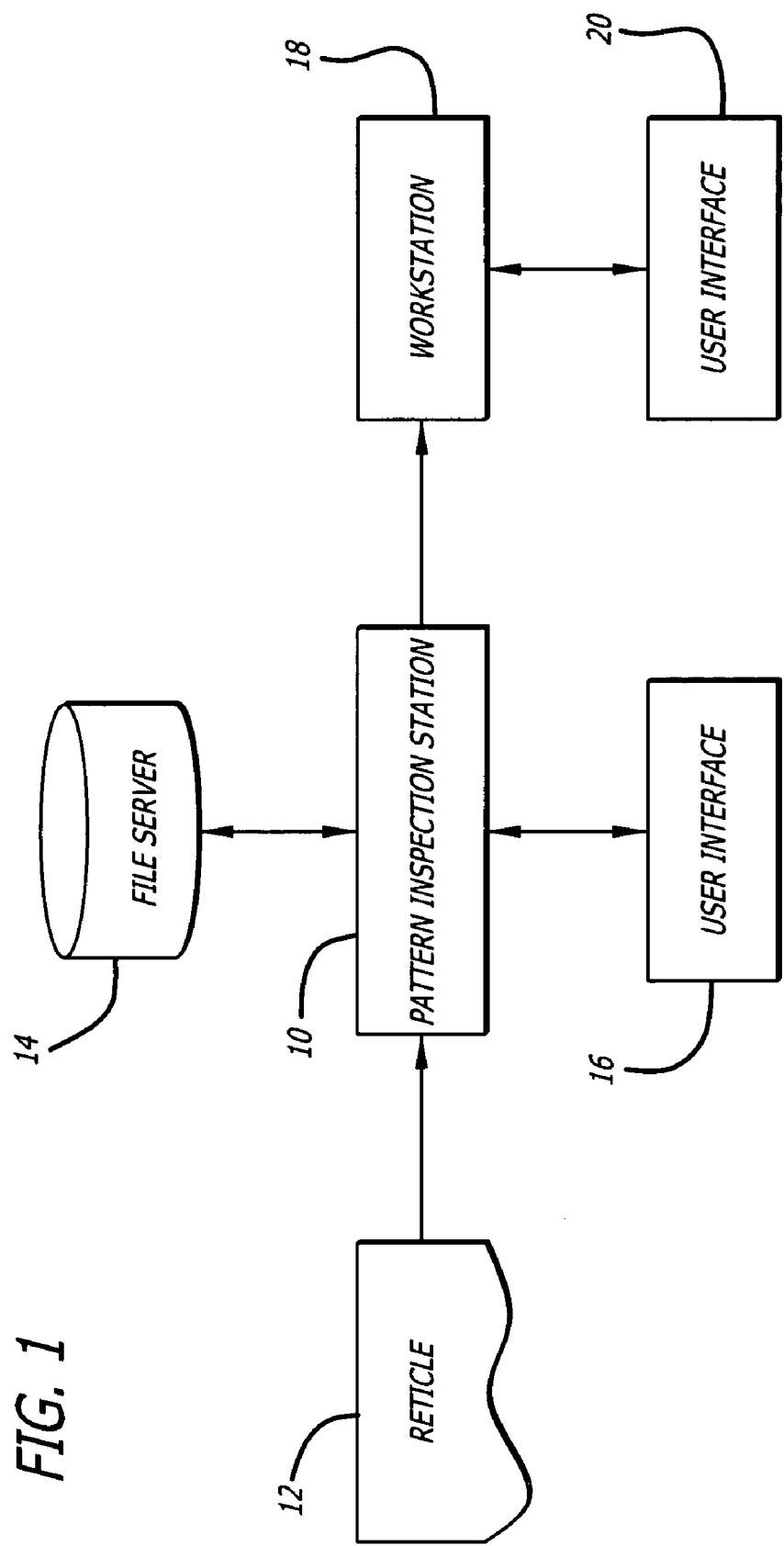
FIG. 1 is a block diagram illustrating a system for implementing the present invention.

FIG. 1 illustrates a block diagram of a system implementing the present invention. Included in the system shown in FIG. 1 is a pattern inspection station 10, such as KLA-Tencor 200 or 300 series pattern inspection station. Included within pattern inspection station 10 is a scanner for inputting digital images of reticles, such as a reticle 12. Pattern inspection station 10 also includes program inspection steps for identifying defects, as defined in more detail below.

Connected to pattern inspection station 10 is file server 14, such as a KLA-Tencor 9X file server, for storing and retrieving image data files and program instruction steps. Also connected to pattern inspection station 10 is a user interface 16 which includes input devices such as a mouse and keyboard and output devices such as a CRT monitor and laser printer.

Under the control of inputs from user interface 16, as described in more detail below, pattern inspection station 10 transfers data files to workstation 18 for simulation. Preferably, workstation 18 is a Sun Microsystems workstation. Connected to workstation 18 is a user interface 20 which may have similar inputs and outputs as user interface 16. Alternatively, pattern inspection station 10 and workstation 18 may share a common user interface. The function of each of the foregoing elements is described in more detail in connection with the following discussion of FIG. 2.

Figure 2:
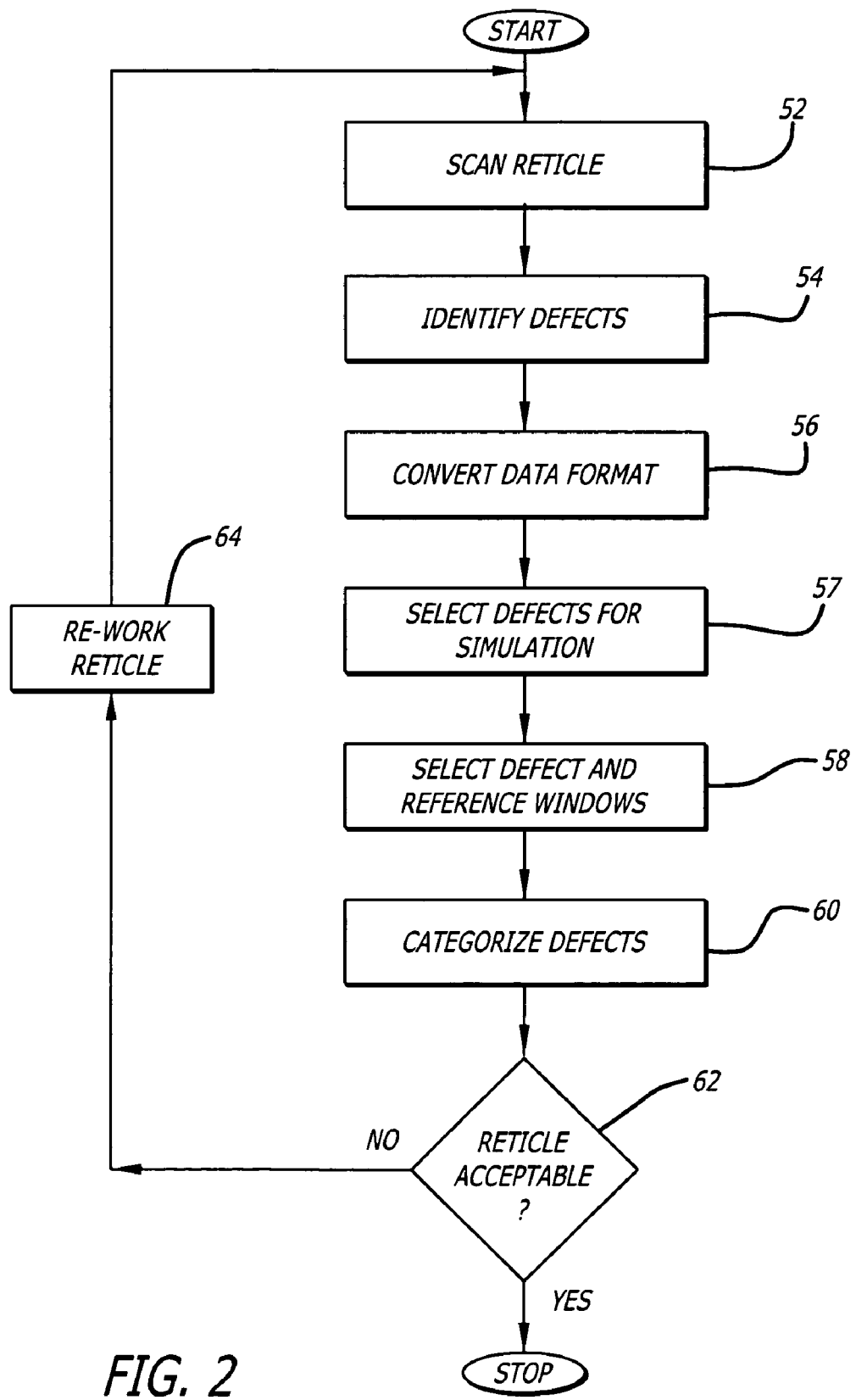
FIG. 2 is a flow diagram illustrating reticle defect identification according to a preferred embodiment of the invention.

FIG. 2 is a flow diagram illustrating detection of defects in a reticle for use in fabrication of an integrated circuit chip, according to a preferred embodiment of the invention. Briefly, according to FIG. 2, a digital image of the reticle is obtained by scanning the reticle; the digital data are processed to identify defects; a user determines which defects merit simulation; the format of the data is converted to facilitate simulation; a response is simulated for each identified portion of the reticle that contains a defect; an operator categorizes each defect based on its simulated image; the user then determines whether the mask is acceptable; if not, the mask may be re-worked; otherwise, processing is complete.

In more detail, in step 52 a digital image of the reticle is generated by scanning the reticle, such as in pattern inspection station 10. Preferably, this scanning process is performed using a laser scanner, such as described by Emery et al. in U.S. Pat. No. 5,737,072 ("Automated Photomask Inspection Apparatus and Method") and by Wihl et al. in U.S. Pat. No. 5,572,598 ("Automated Photomask Inspection Apparatus"), which patents are incorporated herein by reference as though set forth herein in full. As a result of this scanning process, raster image data are generated for the reticle. In the preferred embodiment, each pixel in such raster image data is quantified to an eight-bit grayscale value.

In step 54, the digital image data generated in step 52 are analyzed using a sequence of predetermined processing steps in order to identify defects. In the preferred embodiment, these steps are implemented on a pattern inspection station 10. Such automatic determination of defects can be accomplished in the same manner as described above for conventional techniques.

In the preferred embodiment, this step is executed simultaneously with, and on the same machine as, the reticle scanning of step 52. As each defect is identified, a window of image data that includes the defect is saved. The remainder of the scanned data (i.e., the data not containing a defect) is discarded. Typically, the window saved for each defect is 64×64 pixels with the defect located approximately in the center of the window. However, the window size can be varied based on the sizes of defects and of each pixel. Preferably, however, the window size is chosen large enough so that the subsequent simulation of the window image data is valid in a region near the defect.

Also, in the preferred embodiment, a separate file is created for each defect. Preferably, in addition to the window containing the defect, the file also includes a corresponding window taken from a reference image, which includes the same component features as the defect window but does not include the defect. As noted above, the reference image may be taken from another portion of the reticle, from a different reticle, or from a database which includes an idealized representation of the reticle. Finally, the file preferably also includes certain header information, such as an identification code for the defect, as well as the location of the window in the overall reticle.

In step 56, an image of the window for each defect is displayed to the user, together with an image of the corresponding reference window, on a video monitor in user interface 16. The user evaluates the image of each defect in comparison to the reference image corresponding to that image, and may also or instead view an image formed as the difference between those two images. After reviewing those images, the user can classify the image as problematic, as insignificant or as borderline. If the defect is borderline, it is designated for simulation. It is also noted that more than three different types of classifications may also be used. In any event, if the user is unsure of the appropriate classification for a particular defect, he may designate that defect for simulation.

In step 57, for each defect designated in step 56 the format of the image data for that defect is converted into a format that will facilitate simulation. While not necessary in all embodiments of the invention, this step may be required where one intends to use off-the-shelf simulation programs that use a different data format than is used by the scanner/defect identifier. In the preferred embodiment of the invention, this is the case and, therefore, the raster image data output from step 56 is converted into Sun raster image format.

In step 58, a simulated response is generated for each designated defect window and its corresponding reference window. Preferably, this step simulates an aerial image which would be produced by the subject window. However, it should be noted that other types of lithographic responses may instead be simulated, including for example, aerial image together with resist processing. As noted above, it is preferable to use an off-the-shelf simulation program for this step. In this regard, simulation of the lithographic process has been in use for many years now. In fact, mathematical equations describing the basic steps of the lithography process were proposed as early as 1975. See F. H. Dill, "Optical Lithography," *IEEE Trans. Electron Devices*, ED-22, No. 7, (1975) pp. 440–444; F. H. Dill, W. P. Hornberger, P. S. Hauge, and J. M. Shaw, "Characterization of Positive Photoresist," *IEEE Trans. Electron Devices*, ED-22, No. 7, (July, 1975) pp. 445–452; K. L. Konnerth and F. H. Dill, "In-Situ Measurement of Dielectric Thickness During Etching or Developing Processes," *IEEE Trans. Electron Devices*, ED-22, No. 7, (1975) pp. 452–456; F. H. Dill, A. R. Neureuther, J. A. Tuttle, and E. J. Walker, "Modeling Projection Printing of Positive Photoresists," *IEEE Trans. Electron Devices*, ED-22, No. 7, (July, 1975) pp. 456–464. Moreover, lithography modeling programs have been in use at least since 1979. See W. G. Oldham, S. N. Nandgaonker, A. R. Neureuther and M. O'Toole, "A General Simulator for VLSI Lithography and Etching Processes: Part I—Application to Projection Lithography," *IEEE Trans. Electron Devices*, ED-26, No. 4, (April, 1979) pp. 717–722.

Present lithography simulation techniques model the lithographic system based on specified defocus and lens aberrations, a specified illumination model (e.g., uniform circle or annular), the wavelength of the exposure light, and the range of angles striking the photoresist (as determined by the numerical aperture). The models used in conventional aerial image simulators are based either on scalar diffraction theory or vector diffraction theory. The models based on scalar theory usually follow the analysis of Hopkins. See H. H. Hopkins, "On, the Theory of Optical Images," Proc. Roy. Soc. Ser. A 217, (London, 1953) pp. 408–432. In Hopkins's analysis, light intensity is propagated through the optical system. The mask plane is treated as a partially coherent source surface, and a coherent transfer function describes how a point source in the mask plane is imaged in the plane of the resist. The second group of models (i.e., those based on vector diffraction theory) generally follow the work of Yeung, who traces vector electric fields through the optical system onto the photoresist surface. See M. S. Yeung, "Modeling High Numerical Aperture Optical Lithography," Proc. SPIE 922, (1988) pp. 149. In Yeung's analysis, each ray emanates from a particular source point and travels through a different portion of the mask and the optical system. One advantage of this method is the possibility of application of the Fast Fourier Transform (FFT) in the calculation of coherent images from each source point. The electric field at the resist surface due to that source point can be obtained by integration over the solid angles subtended by the optical system.

Prior to the present invention, lithography simulation programs have been used mainly for reticle design, in which a reticle is designed on a CADS and the simulator then simulates the aerial image that would be produced by a proposed design. Based on the simulation results, the designer might modify the design, such as by adding OPC elements to correct observed diffraction effects. Because the existing simulators were used for design, they often will require a certain amount of modification for dealing with scanned in image data for an actual reticle, rather than reticle design data. For instance, design data light transmission values generally can be represented as binary numbers, signifying 100% or 0% transmission, whereas the optical image of a reticle includes grayscale values, particularly near feature edges where a pixel may overlap both a transmissive and a non-transmissive region. Other exemplary modifications are described below, and still others will be apparent to this skilled in the art.

In the preferred embodiment, Numerical Technologies, Inc.'s Virtual Stepper software (with the modifications described herein) is used for simulating the photolithographic response of the individual windows. Such software typically is sold as a package and can be installed on any general purpose computer having the specified minimum requirements. In the preferred embodiment, the simulation software is run on a Sun Microsystems workstation. The input digital image data are downloaded directly from the pattern inspection station 10 to workstation 18 upon a user command input via user interface 16. It is noted that it is also possible to instead use a modified version of Avant!'s simulation software Progen or any of a number of other simulation software packages.

Because an off-the-shelf reticle design simulator is used in the preferred embodiment, prior to actual simulation the image data typically must be pre-processed to match the simulator's required input resolution and quantization range. In the preferred embodiment, scaling is done linearly and magnification (resolution matching) is performed by interpolating between the sample values. Upon completion of simulation processing, the results are displayed to the user via user interface 20.

Preferably, the data displayed to the user is in the form of an image representing the projected aerial image. However, it should be understood that the data may be presented to the user in any other form. Typically, displayed on user interface 20 will be an aerial image for the defect window and for the reference window. However, the invention also contemplates displaying an image formed as the difference between those two images.

In step 60, the user evaluates the simulation data for each window and categorizes the defect in the window. In this regard, a user might determine that the defect will not print on the die. Alternatively, even if the defect prints on the die, the user might determine that the print is in the non-critical portion of the circuit and therefore will not be a problem. Finally, the user might determine that the defect causes a print which is likely to cause a circuit failure. In this step also, it is possible to use more than three different types of characterizations.

In step 62, the user determines whether the reticle is acceptable based on his previous defect categorizations. If the reticle is acceptable, then processing is completed. Otherwise, the reticle may be reworked in step 64 in order to attempt to correct the defect; in this case, the reworked reticle is then re-scanned in step 52 and the process repeats.

Figure 3A:
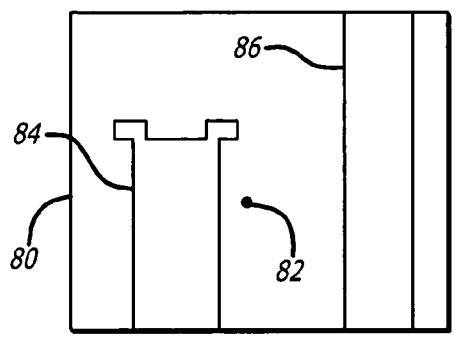
FIGS. 3A and 3B illustrate a subject image window including a defect and a reference window corresponding to a subject window, respectively.
Figure 3B:
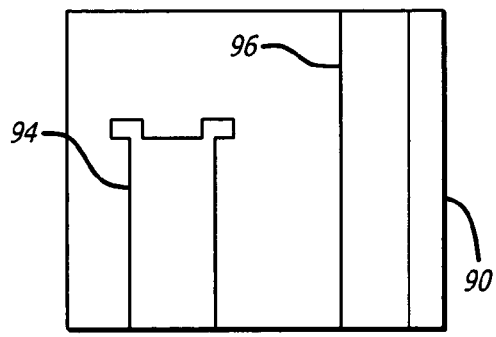

An example of the foregoing processing will now be described with reference to the illustrations shown in FIGS. 3 through 6. Specifically, FIG. 3A illustrates a window 80 which includes a detected defect 82 and also includes reticle elements 84 and 86. FIG. 3B illustrates a reference window corresponding to window 80. In FIG. 3B element 94 is identical to element 84 and element 96 is identical to element 86. However, FIG. 3B does not include a defect such as defect 82.

Figure 4A:
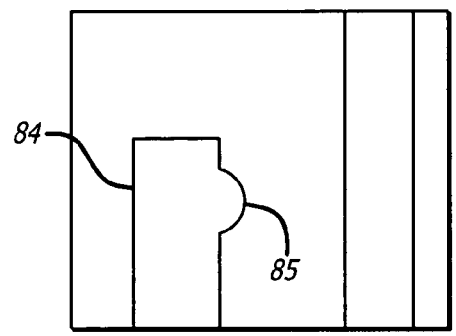
FIGS. 4A and 4B illustrate the results after simulation processing of the images shown in FIGS. 3A and 3B, respectively.
Figure 4B:
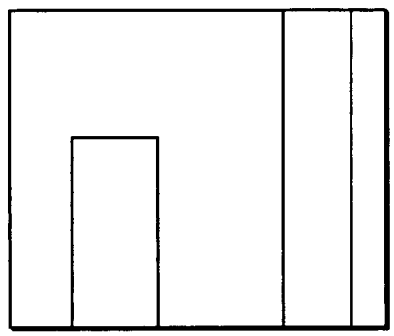

In this case, the user is uncertain as to the effect of defect 82. Accordingly, he designates window 80 (and its corresponding reference window 90) for simulation. FIGS. 4A and 4B illustrate the simulation results after processing windows 80 and 90, respectively. As shown in FIG. 4A, defect 82 has resulted in a bulge 88 in element 84. Based on the image shown in FIG. 4A, the user can determine whether defect 82 is problematic. In making this determination, the image shown in FIG. 4B which corresponds to the reference data may be helpful.

Figure 5A:
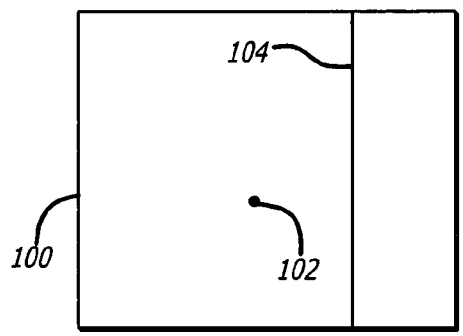
FIGS. 5A and 5B illustrate a different subject image window including a defect and a reference window corresponding to a subject window, respectively.
Figure 5B:
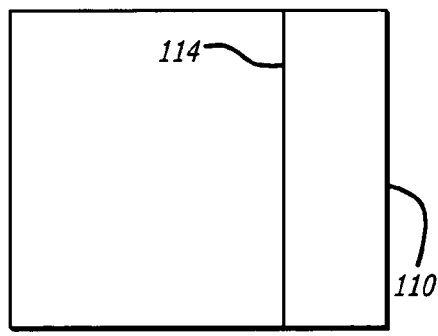

FIGS. 5 and 6 illustrate a further example of such processing. Specifically, FIG. 5A illustrates a window 100 which includes defect 102 and reticle element 104. FIG. 5B illustrates window 110 which is the image data corresponding to window 100. As shown in FIG. 5B, window 110 includes element 114, which corresponds to element 104 in FIG. 5A. However, window 110 does not include a defect corresponding to defect 102.

Figure 6A:
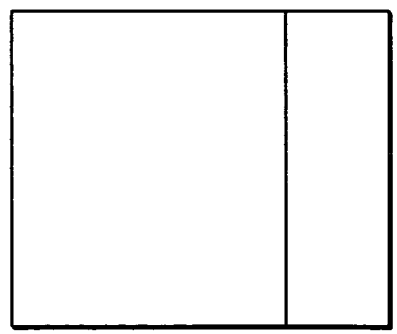
FIGS. 6A and 6B illustrate the results after simulation processing of the images shown in FIGS. 5A and 5B, respectively.
Figure 6B:
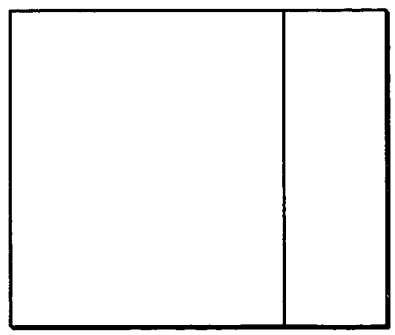

FIGS. 6A and 6B illustrate the simulation results corresponding to FIGS. 5A and 5B, respectively. As shown in FIG. 6A, defect 102 has failed to print. Accordingly, FIGS. 6A and 6B are virtually identical. As a result, the user will characterize defect 102 as being insignificant.

By providing a simulation of each borderline reticle defect, the present invention generally can provide a user with additional information which can be used to more accurately characterize reticle defects. Because defects are characterized more accurately, the present invention often can avoid many user errors. As noted above, accurate information regarding defect characterizations is critical to avoid late discovery of problematic defects and also to avoid unnecessary re-working innocuous defects.

Although the present invention has been described in detail with regard to the exemplary embodiments and drawings thereof, it should be apparent to those skilled in the art that various adaptations and modifications of the present invention may be accomplished without departing from the spirit and the scope of the invention. Accordingly, the invention is not limited to the precise embodiments shown in the drawings and described in detail above. Therefore, it is intended that all such variations not departing from the spirit of the invention be considered as within the scope thereof as limited solely by the claims appended hereto.

For instance, the invention may also be modified to include the additional step, after simulation processing, of automatically characterizing defects based on the simulation data. Such characterizations may be made, for example, based on the change in the local critical dimension as a result of the defect. Alternatively, the defect may be automatically characterized by measuring the change in illumination energy as a result of the defect.

Also, while the preferred embodiment has been described above, it should be apparent to those skilled in the art that the present invention also contemplates using simulation in conjunction with other defect detection techniques. For instance, such simulation also may used in the techniques described in U.S. Pat. Nos. 5,619,588 and 5,619,429, which patents are incorporated herein by reference as though set forth herein in full.

In the following claims, those elements which do not include the words "means for" are intended not to be interpreted under 35 U.S.C. § 112 ¶ 6.

What is claimed is:

1. A method for detecting defects in a reticle used in integrated circuit chip fabrication, said method comprising:
   (a) obtaining digital image data corresponding to an image of a reticle;
   (b) processing the digital image data according to predetermined criteria to identify defects; and
   (c) simulating a response that would be produced if the reticle were to be utilized in a photolithographic system, by processing the digital image data corresponding to the reticle.

2. A method according to claim 1, wherein the digital image data are obtained by scanning the reticle.

3. A method according to claim 1, wherein the defects are identified in step (b) by comparing the digital image data to reference digital image data.

4. A method according to claim 1, wherein step (c) simulates an aerial image which would be produced by the reticle.

5. A method according to claim 1, further comprising a step of categorizing defects based on simulation results produced in step (c).

6. A method according to claim 1, wherein the digital image data are in raster format.

7. A method according to claim 1, further comprising a step of modifying a format of the digital image data prior to performing step (c).

8. A method according to claim 1, further comprising a step of providing a reference simulation for comparison to a simulation produced in step (c).

9. A method for detecting defects in a reticle used in integrated circuit chip fabrication, said method comprising:
   (a) obtaining digital image data corresponding to an image of a reticle;
   (b) processing the digital image data according to predetermined criteria to identify defects;
   (c) specifying a window around one of the defects identified in step (b); and
   (d) simulating a response that would be produced if the window specified in step (c) were to be utilized in a photolithographic system, by processing digital image data corresponding to the window specified in step (c).

10. A method according to claim 9, wherein the digital image data are obtained by scanning the reticle.

11. A method according to claim 9, wherein step (d) simulates an aerial image which would be produced by the window.

12. A method according to claim 9, further comprising a step of categorizing defects based on simulation results produced in step (d).

13. A method according to claim 9, further comprising a step of simulating a window of corresponding reference image data for comparison to simulation results produced in step (d).

14. A method according to claim 9, wherein the window is 64×64 pixels.

15. A method according to claim 9, wherein the digital image data processed in step (d) are grayscale data.

16. A method according to claim 9, wherein the defects are identified in step (b) by comparing the digital image data to reference digital image data.

17. A computer-readable medium having encoded thereon computer-executable process steps, said process steps for detecting defects in a reticle used in integrated circuit chip fabrication, wherein said process steps comprise steps to:
   (a) obtain digital image data corresponding to an image of a reticle;
   (b) process the digital image data according to predetermined criteria to identify defects; and
   (c) simulate a response that would be produced if the reticle were to be utilized in a photolithographic system, by processing the digital image data corresponding to the reticle.

18. A computer-readable medium according to claim 17, wherein said computer readable medium comprises at least one of a magnetic diskette, magnetic tape, a CD-ROM, a random access memory chip, and a read-only computer memory chip.

19. A computer-readable medium having encoded thereon computer-executable process steps, said process steps for detecting defects in a reticle used in integrated circuit chip fabrication, said process steps comprising steps to:
   (a) obtain digital image data corresponding to an image of a reticle;
   (b) process the digital image data according to predetermined criteria to identify defects;
   (c) specify a window around one of the defects identified in step (b); and
   (d) simulate a response that would be produced if the window specified in step (c) were to be utilized in a photolithographic system, by processing digital image data corresponding to the window specified in step (c).

20. A computer-readable medium according to claim 19, wherein said computer readable medium comprises at least one of a magnetic diskette, magnetic tape, a CD-ROM, a random access memory chip, and a read-only computer memory chip.

21. An apparatus for detecting defects in a reticle used in integrated circuit chip fabrication, said apparatus comprising:
   a processor for executing stored program instruction steps; and
   a memory connected to the processor for storing the program instruction steps,
   wherein the program instruction steps include steps to:
      (a) obtain digital image data corresponding to an image of a reticle;
      (b) process the digital image data according to predetermined criteria to identify defects; and
      (c) simulate a response that would be produced if the reticle were to be utilized in a photolithographic system, by processing the digital image data corresponding to the reticle.

22. An apparatus for detecting defects in a reticle used in integrated circuit chip fabrication, said apparatus comprising:
   a processor for executing stored program instruction steps; and
   a memory connected to the processor for storing the program instruction steps,
   wherein the program instruction steps include steps to:
      (a) obtain digital image data corresponding to an image of a reticle;
      (b) process the digital image data according to predetermined criteria to identify defects;
      (c) specify a window around one of the defects identified in step (b); and
      (d) simulate a response that would be produced if the window specified in step (c) were to be utilized in a photolithographic system, by processing digital image data corresponding to the window specified in step (c).

* * * * *